United States Patent [19]

Angstadt

[11] 4,247,478
[45] Jan. 27, 1981

[54] PROCESS AND CATALYST FOR HYDROGENATION OF AROMATIC DINITRILES

[75] Inventor: Howard P. Angstadt, Media, Pa.

[73] Assignee: Suntech, Inc., Philadelphia, Pa.

[21] Appl. No.: 95,189

[22] Filed: Nov. 16, 1979

[51] Int. Cl.$^3$ .............................................. C07C 85/12
[52] U.S. Cl. ................................... 564/422; 252/472; 564/428
[58] Field of Search .................. 260/570.5 P, 570.9, 260/578, 583 K

[56] References Cited

U.S. PATENT DOCUMENTS

| | | | |
|---|---|---|---|
| 2,165,515 | 7/1939 | Schmidt | 260/570.9 X |
| 2,953,490 | 9/1960 | Deebel | 260/570.9 P |
| 3,110,747 | 11/1963 | Mullineaux | 260/570.9 X |
| 3,117,162 | 1/1964 | Rylander et al. | 260/570.9 X |
| 3,152,184 | 10/1964 | Levering | 260/570.9 |
| 3,558,709 | 1/1971 | Hockele | 260/578 X |
| 3,847,989 | 11/1974 | Platz et al. | 260/570.9 |
| 4,140,720 | 2/1979 | Drake | 260/583 P |
| 4,163,025 | 7/1979 | Plunkett et al. | 260/570.9 |
| 4,186,146 | 1/1980 | Dutte et al. | 260/570.5 P |

FOREIGN PATENT DOCUMENTS

| | | | |
|---|---|---|---|
| 2603006 | 7/1976 | Fed. Rep. of Germany | 260/570.9 |
| 39-28638 | 10/1964 | Japan | 260/578 |
| 42-8303 | 8/1967 | Japan | 260/570.9 |
| 925457 | 5/1963 | United Kingdom | 260/570.9 |
| 183764 | 8/1966 | U.S.S.R. | 260/570.9 |
| 345139 | 8/1972 | U.S.S.R. | 260/578 |

OTHER PUBLICATIONS

Bizhanov et al., "Chemical Abstracts" vol. 65, Ab. No.20038a (1966.

*Primary Examiner*—John Doll
*Attorney, Agent, or Firm*—J. Edward Hess; Donald R. Johnson; Paul Lipsitz

[57] ABSTRACT

In the process of hydrogenating an aromatic dinitrile to the corresponding di-primary amine in the presence of a catalyst, the improvement of using as catalyst a cobalt catalyst promoted with rhodium where the weight ratio of rhodium to cobalt is 1.0 or less.

11 Claims, 5 Drawing Figures

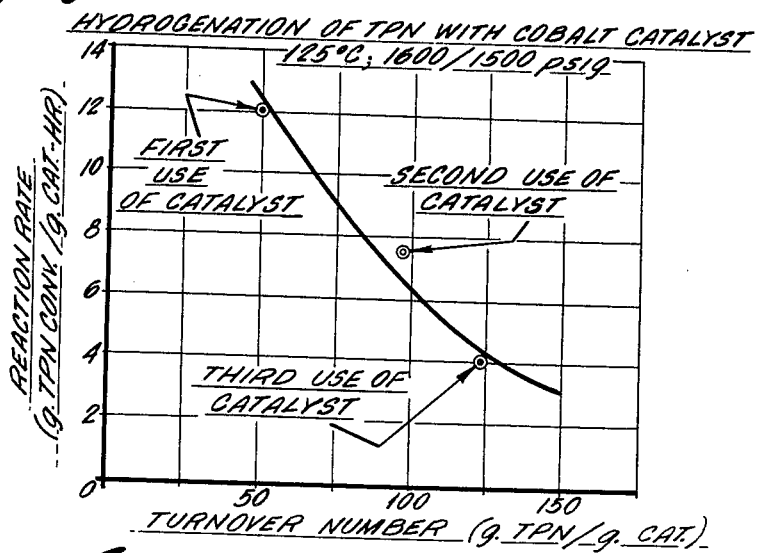
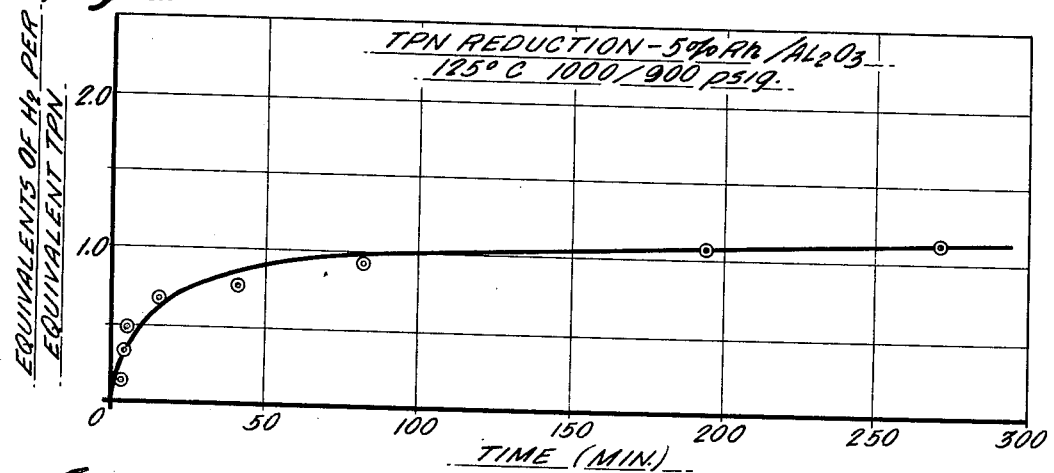
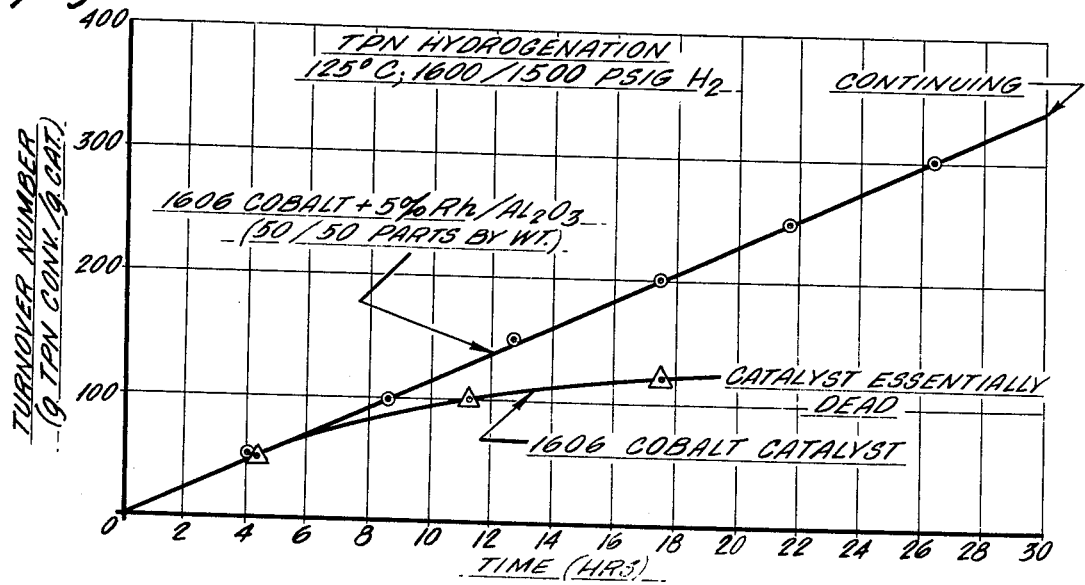

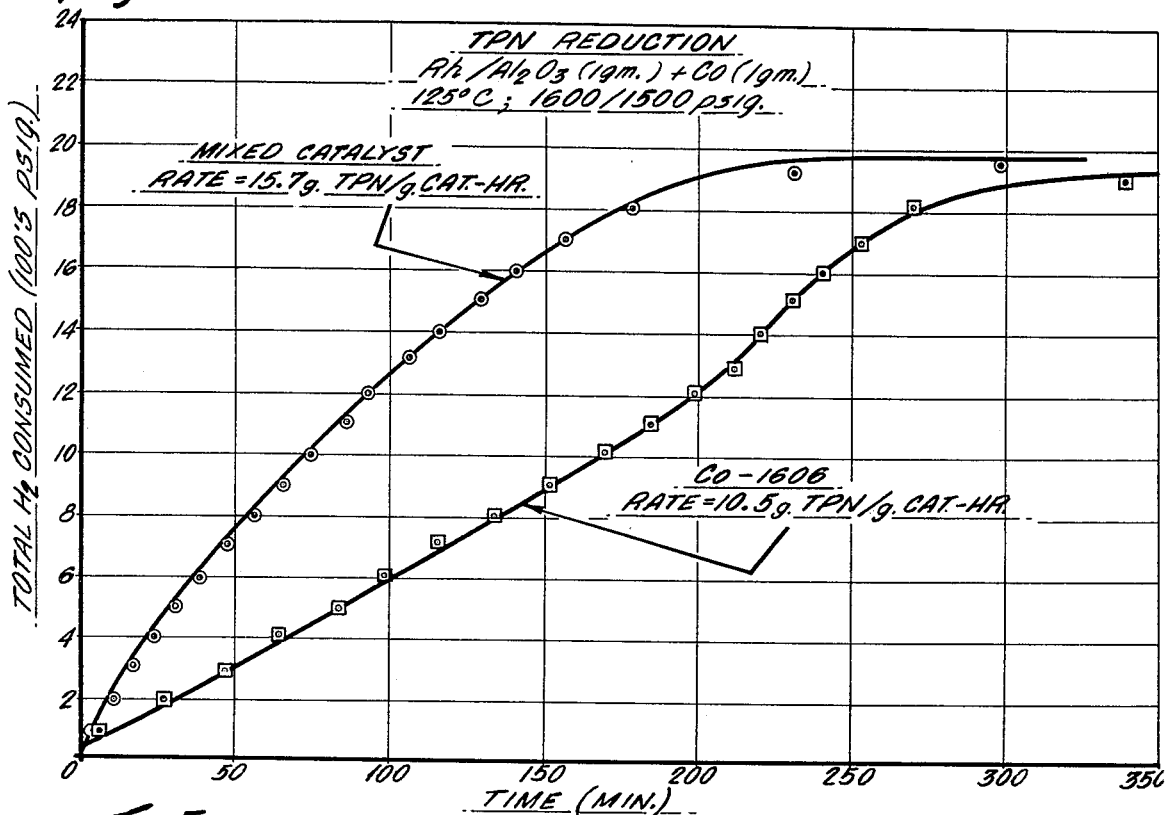
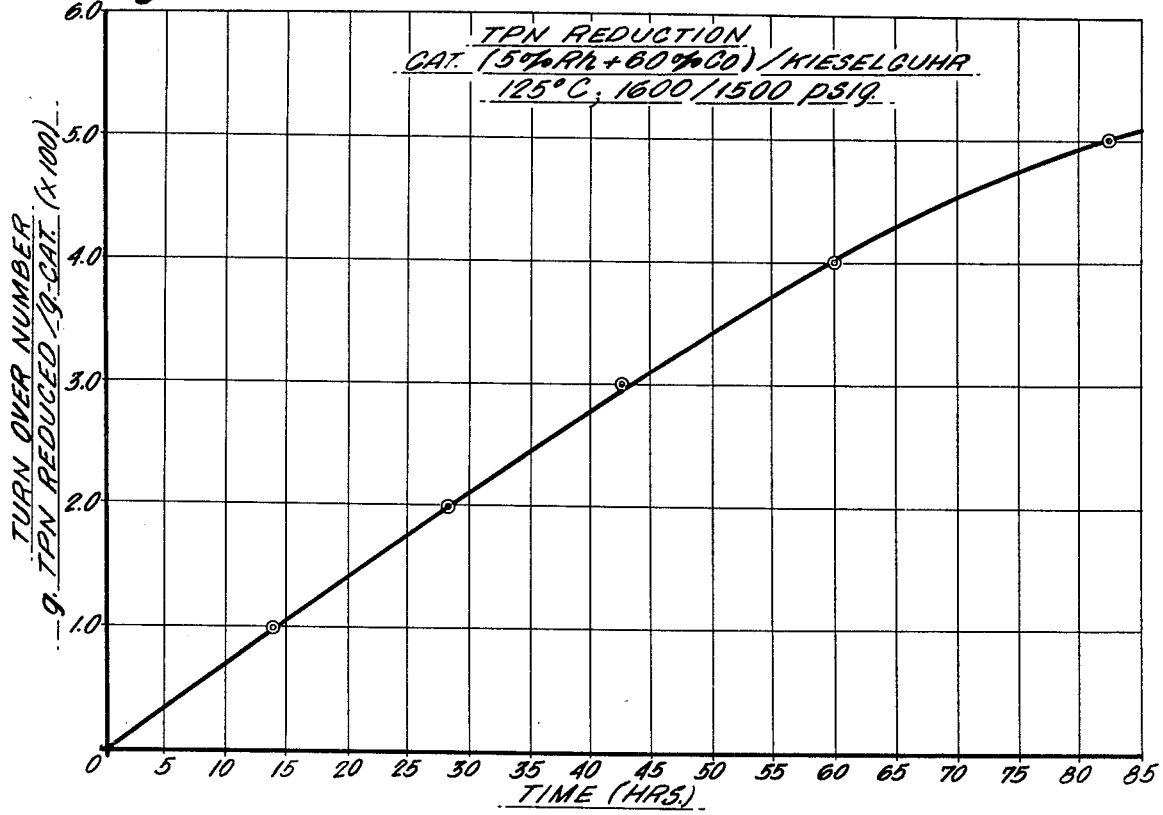

PROCESS AND CATALYST FOR HYDROGENATION OF AROMATIC DINITRILES

It is known in the art to hydrogenate aromatic dinitriles to di-primary amines and numerous catalysts have been disclosed for such process. In U.S. Pat. No. 3,117,162 rhodium and other platinum metal catalysts on various supports are disclosed for hydrogenation of nitriles. U.S. Pat. No. 3,255,248 discloses a sintered cobalt (or nickel) oxide catalyst for nitrile hydrogenation. British Patent 1,149,251 discloses a mixture of a major amount of cobalt and a minor amount of zirconium as catalyst for dinitrile hydrogenation to di-primary amines. A mixed catalyst of rhodium and platinum is said to be most effective for aromatic dinitrile hydrogenation in an article by Yuzuru Takagi et al (Sci, Papers I.P.C.R. V. 61 (3): 1967). A similar disclosure where ruthenium combined with platinum, palladium or rhodium is shown to be a catalyst for nitrile and other hydrogenation is found in U.S. Pat. No. 3,177,258. U.S. Pat. No. 3,350,455 discloses a two step process for converting aliphatic dinitriles to the diamines by first ozonizing and then reducing the ozonide with hydrogen using a cobalt or rhodium catalyst.

In the case of catalysts such as the so-called skeletal cobalt catalyst (e.g. 85% metallic cobalt plus binders; Harshaw 1606) reduction of the aromatic dinitrile to the diamine is quite selective (i.e. few by-products), but catalyst life is quite short. In the case of catalysts such as supported rhodium (e.g. 5% rhodium on alumina) the reduction of the aromatic dinitrile is very rapid initially, but proceeds only to about one-quarter of completion. Thus, the end product contains mostly unreacted nitrile and partially reacted nitrile.

It has now been found that those disadvantages of cobalt and rhodium catalysts in aromatic dinitrile hydrogenation are overcome by using as catalyst for the reaction a rhodium promoted cobalt catalyst where the weight ratio of rhodium to cobalt is no greater than 1.0.

FIG. 1 shows certain data for the prior art reduction of terephthalonitrile with a cobalt catalyst.

FIG. 2 shows data for the prior art reduction of terephthalonitrile with a rhodium catalyst.

FIGS. 3, 4 and 5 show data for the reduction of terephthalonitrile with various rhodium promoted cobalt catalysts in accord with the invention.

The general procedure for the hydrogenation of the aromatic nitriles is well known in the art and the mixed catalyst will be employed in the conventional manner. However, a preferred embodiment of the invention involves carrying out the hydrogenation of an aromatic dinitrile, preferably of the benzene and naphthalene series, in a solvent system comprising an ether, ammonia and an amount of water of from about 10% to about 20% by volume of the total solvent used (i.e., ether plus water). Such a system is described in Ser. No. 8,310, filed Feb. 1, 1979 (Allowed).

In this preferred process of the invention a mixture of the solvent, nitrile, ammonia, water and catalyst is heated to a reaction temperature of from about 85° C. to about 150° C., preferably about 115° to about 125° C. and hydrogen introduced, with stirring, to a hydrogen pressure of from about 500 to about 3000 psig. The reaction is allowed to proceed until hydrogen uptake ceases or until aliquot samples show that all of the nitrile has been converted. Then, the reactor is cooled and vented and the contents are removed and filtered to recover the catalyst. The filtrate is distilled to recover solvent and the product is distilled under reduced pressure.

The process may be carried out in the usual equipment for such reactions and will be, preferably, a continuous trickle bed reactor. With such equipment the nitrile solution and hydrogen are passed thru a catalyst bed and the catalyst is present in large excess over the nitrile contained in the reaction zone.

The hydrogenation of dinitrile to diamine may be carried out with a wide variety of aromatic dinitriles, but as indicated, will preferably employ those of the benzene or naphthalene series such as phthalonitrile, isophthalonitrile, terephthalonitrile, 1,2-, 2,3- 1,4-, 1,6-, 2,6- or 1,8-dicyanonaphthalene and the like. It will be understood that the aromatic ring may have substituents such as lower alkyl (methyl, ethyl, butyl, etc.), halogen, alkoxy, and similar groups inert to the hydrogenation.

The solvent used will be an ether or a polyether (di- or tri-preferred) preferably with 4 to 6 carbon atoms and a carbon to oxygen ratio of from 2:1 to 5:1. Cyclic ethers such as dioxane, and tetrahydrofuran are useful as are acyclic ethers exemplified by ethylene glycol dimethyl ether and diethylene glycol dimethyl ether. The preferred solvent is diethylene glycol dimethyl ether.

The amount of ammonia in the reaction mass will be from about 5% to about 30% by volume of the solvent. The ammonia is believed to be helpful in suppressing the formation of unwanted secondary and tertiary amine by-products.

The presence of a specific amount of water in the reaction mass is of value in obtaining optimum results for the process. Frequently, polymeric or oxygen containing by-proucts products result when the hydrogenation of a nitrile is carried out in an aqueous system containing ammonia. However, by controlling the amount of water to from about 10% to about 20% by volume of the total solvent used (i.e., ether plus water), the product is the desired primary amine in high yield. A further advantage of the effect of the specific amount of water in the reaction mass is that the reaction rate is significantly enhanced at a water concentration of about 10%. More than 20% of water gives a further slight increase in reaction rate, but the yield of desired product falls off. A still further advantage of the presence of water in the process is that yields of product remain high when the catalyst is recycled.

The yield of di-primary amines produced in the process declines as the concentration of nitrile in the solvent is increased. In general, satisfactory results are obtained with up to about 25% nitrile by weight based on solvent. Lower concentrations are preferred, but practical considerations will normally dictate about 5% as the lower limit.

The cobalt catalyst is a conventional cobalt hydrogenation catalyst. One useful type may be a skeletal catalyst such as Raney cobalt. Another useful catalyst may be of the type where cobalt is supported on a support such as alumina, silica, kieselguhr, silica-alumina and the like. Generally from about 5% to about 20% by weight of catalyst and support will be cobalt. Preferably, the supported catalyst will be prereduced with hydrogen to convert the oxide to metallic cobalt, and, where used, will have kieselguhr, a silica and/or an alumina type binder. These catalysts are commercially available and are typified by Harshaw 1606.

The rhodium used to promote the cobalt catalyst may itself be, preferably, a conventional type catalyst comprising rhodium (or its oxide) on a support, preferably alumina.

As indicated, the weight ratio of rhodium to cobalt must be 1.0 or less since it has been found that above this ratio only partial reduction of the dinitrile is obtained. A ratio as low as about 0.1 appears effective, but, in general, ratios of from about 0.2 to 1.0 will be employed. Specific ratios of 0.2, 0.33, 0.5 and 0.66 have been found to be particularly suitable.

It is also of interest that when the cobalt is replaced by nickel, the dinitrile reduction according to the invention is not effective. In view of the similarity of catalytic function of nickel and cobalt it is surprising that only rhodium promoted cobalt catalysts are operable in this invention.

Several alternative procedures may be used to make the catalyst for use in the invention. One procedure is simply to mix the conventional cobalt and rhodium catalysts in the desired proportion. While not a preferred technique, this method does give an increased rate of reaction and increased catalyst life.

A somewhat better procedure is to impregnate a supported cobalt catalyst with a soluble rhodium salt, evaporate the solvent and calcine. The amount of rhodium put on the supported cobalt catalyst will vary dependent upon the amount of cobalt present, but, preferably, the amount of rhodium will be about 3% to 35% by weight of the cobalt. A mixed catalyst prepared in this way gives increased life, although when the rhodium content is low (2% to 5%) reaction rate may be reduced slightly. At higher rhodium loadings of about 15% to 35% the reaction proceeds at a very fast rate and enables a high catalyst longevity to be obtained.

A preferred catalyst for the process is made by impregnating a cobalt catalyst supported on kieselguhr. The kieselguhr will contain about 60% by weight of cobalt and this is impregnated with rhodium chloride in an amount to give a weight ratio of rhodium to cobalt of 1:3 (i.e. 0.33). Then the impregnated kieselguhr support is heated in air at about 700° C. for about four hours to yield the rhodium promoted cobalt catalyst which will contain about 51% cobalt and about 17% rhodium.

In order to illustrate the invention reference is made to the following examples.

GENERAL PROCEDURE

A stirred autoclave is charged with 900 ml. of diethylene glycol dimethyl ether (Diglyme), 100 ml. ammonia, 100 g. terephthalonitrile (TPN) and the desired amount of catalyst and 100 ml of water. The autoclave is heated to 125° C. Hydrogen is introduced rapidly until the selected pressure is reached. The absorption of hydrogen starts immediately and additional hydrogen is added to keep the pressure at the selected level. The course of the reaction is monitored by measuring the volume of hydrogen consumed and by periodic withdrawal of a small sample of the reaction mixture for analysis. When the analysis indicates that all of the terephthalonitrile is reacted, the agitation is stopped and the reactor is cooled rapidly and vented. The reaction mixture is filtered to recover the catalyst and then is flash evaporated to remove solvent. The residual oil is distilled at about 100° C. and 0.5 mm Hg. to give practically pure p-xylene diamine. A small amount of high rolling residue remains in the distillation pot.

Reference is now made to the figures.

FIG. 1 indicates the results obtained upon hydrogenation of terephthalonitrile (TPN) with a cobalt catalyst (Harshaw 1606) used three successive times at 125° C. at pressures of 1600 to 1500 psig. As can be seen, each time the catalyst was reused the rate of reaction decreased rapidly and after approximately 150 turnovers (e.g. grams of nitrile converted per gram of catalyst) the rate had decreased to about one-fourth its original value, thus indicating a very short catalyst life.

FIG. 2 shows the hydrogen uptake rate for TPN reduction with a conventional rhodium catalyst supported on alumina. As can be seen, although uptake is originally rapid, it quickly levels off to a point where only about one equivalent of hydrogen is reacted per equivalent of TPN rather than the four equivalents required for complete reaction. Thus, in this system only about one-fourth of the available nitrile groups would be hydrogenated.

FIG. 3 illustrates the invention as carried out with a rhodium promoted cobalt catalyst where the cobalt catalyst is mixed with a rhodium catalyst supported on alumina. For comparison, a cobalt catalyst alone is also shown. As can be seen, after 26 hours the reaction with the rhodium-cobalt catalyst is still continuing to function whereas with the cobalt catalyst alone, the catalyst is essentially dead after 18 hours.

As shown in FIG. 3 the turnover number for the rhodium promoted cobalt catalyst is about 300. Turnover number is the grams of nitrile reduced per gram of catalyst and reflects the number of times the catalyst can be reused without regeneration and is thus a measure of catalyst life.

FIG. 4 compares the rate of TPN hydrogenation using the rhodium-cobalt catalyst with that of a skeletal cobalt catalyst. As can be seen the promoted catalyst provides an increase in rate which is 50% above that obtained with the cobalt alone.

FIG. 5 shows the results obtained with a preferred catalyst where the rhodium is impregnated on the supported cobalt catalyst. As can be seen the turnover number for the catalyst is over 500, a very significant and important property for commercial use of the catalyst.

Table 1 shows the results obtained with a commercially available, kieselguhr supported cobalt catalyst impregnated with rhodium as described above comprised of 17% by weight rhodium of 51% cobalt. As can be seen from the data, an average hydrogenation rate of 18.9 g. TPN converted per gram catalyst-hour is obtained. The turnover number for this catalyst is over 1000. Thus, both the rate of reaction and catalyst lifetime have been substantially improved over that observed with either component alone.

Table 2 summarizes the above data for ready comparison and shows the very significant improvement in lifetime obtained with the rhodium promoted catalyst.

TABLE 1

TPN Hydrogenation - Life Study
Cat: (17% Rh + 51% Co)/Kieselguhr - 1g.

| Run No | Absorbed moles $H_2$ Per Run | Total | TPN Grams | PXDA* Moles | Time mins | hrs | Total hrs |
|---|---|---|---|---|---|---|---|
| 1 | 2.81 | | 100 | 0.780 | 441 | 7.35 | 7.35 |
| 2 | 3.64 | 6.45 | 100 | 0.780 | 253 | 4.22 | 11.57 |
| 3 | 3.91 | 10.36 | 100 | 0.780 | 275 | 4.58 | 16.15 |
| 4 | 3.98 | 14.34 | 100 | 0.780 | 331 | 5.52 | 21.67 |
| 5 | 3.75 | 18.09 | 100 | 0.780 | 281 | 4.68 | 26.35 |

TABLE 1-continued

TPN Hydrogenation - Life Study
Cat: (17% Rh + 51% Co)/Kieselguhr - 1g.

| Run No | Absorbed moles $H_2$ Per Run | To-tal | TPN Grams | PXDA* Moles | Time mins | hrs | To-tal hrs |
|---|---|---|---|---|---|---|---|
| 6 | 3.64 | 21.73 | 100 | 0.780 | 358 | 5.97 | 32.32 |
| 7 | 3.92 | 25.65 | 100 | 0.780 | 261 | 4.35 | 36.69 |
| 8 | 3.08 | 28.73 | 100 | 0.780 | 336 | 5.60 | 42.27 |
| 9 | 3.67 | 32.40 | 100 | 0.780 | 312 | 5.20 | 47.47 |
| 10 | 3.52 | 35.92 | 100 | 0.780 | 320 | 5.33 | 52.80 |
| 10 | 35.92 | 35.92 | 1000 | 7.80 | 2968 | 52.80 | 52.80 |
| Average: | 3.59 | 3.59 | 100 | 0.78 | 297 | 5.28 | 5.28 |

Average Rate = 18.9 g. TPN  Turnover number = over 1000
converted/g Cat. - hr.

*PXDA = p-Xylenediamine

TABLE 2

TPN Reduction Catalysts

| Catalyst | Rate (g TPN con/g Cat hr) | Lifetime Turnover Number (g TPN/g Cat) |
|---|---|---|
| 85% Cobalt (Harshaw 1606) | 10.5 | 150 |
| 60% Cobalt/Kieselguhr | 5.2 | (Not Determined) |
| 5% Rhodium/Al$_2$O$_3$ | 18.0 | 25 |
| 5% Rh/Al$_2$O$_3$ + Cobalt (Harshaw 1606) | 15.7 | 400 |
| (5% Rh + 60% Co) Kieselguhr | 6.1 | 500 + |
| (17% Rh + 51% Co) Kieselguhr | 19.9 | 1000 + |

The invention claimed is:

1. In the process of hydrogenating an aromatic dinitrile to the corresponding di-primary amine in the presence of a catalyst, the improvement of using as catalyst a cobalt catalyst promoted with rhodium where the weight ratio of rhodium to cobalt is 1.0 or less.

2. The process of claim 1 wherein the aromatic dinitrile is of the benzene or naphthalene series.

3. The process of claim 2 where the dinitrile is terephthalonitrile.

4. A process for the hydrogenation of terephthalonitrile to p-xylylene diamine which comprises hydrogenating terephthalonitrile at a temperature of from about 85° C. to about 150° C. in the presence of a rhodium promoted cobalt catalyst where the weight ratio of rhodium to cobalt is 1.0 or less.

5. The process of claim 4 wherein the reaction is carried out in an ether or polyether solvent where said ether contains from 4 to 6 carbon atoms and has a carbon to oxygen ratio of from 2:1 to 5:1, said solvent containing ammonia in an amount of from about 10%.

6. The process of claim 5 wherein said ether is diethylene glycol dimethyl ether.

7. A process for the hydrogenation of terephthalonitrile to p-xylylene diamine which comprises hydrogenating terephthalonitrile in the presence of a rhodium promoted cobalt catalyst at a temperature of from about 115° C. to about 125° C. in an ether solvent system where said ether contains from 4 to 6 carbon atoms and has a carbon to oxygen ratio of from 2:1 to 5:1, said solvent containing ammonia in an amount of from about 5% to about 30% by volume of said ether and water in an amount of from about 10% to about 20% by volume of said solvent, and where the weight ratio of rhodium to cobalt in said catalyst is 1.0 or less.

8. The process of claim 7 wherein the solvent is diethylene glycol dimethyl ether.

9. The process of claim 7 wherein the catalyst is comprised of a supported cobalt catalyst promoted with rhodium and containing about 51% cobalt and about 17% rhodium.

10. The process of claim 9 wherein the cobalt catalyst is supported on kieselguhr.

11. The process of claim 7 wherein the catalyst is comprised of cobalt on kieselguhr which has been promoted by impregnation with rhodium.

* * * * *